United States Patent [19]
Goodin

[11] Patent Number: 5,397,307
[45] Date of Patent: Mar. 14, 1995

[54] DRUG DELIVERY PTCA CATHETER AND METHOD FOR DRUG DELIVERY

[75] Inventor: Richard Goodin, Blaine, Minn.

[73] Assignee: Schneider (USA) Inc., Plymouth, Minn.

[21] Appl. No.: 163,852

[22] Filed: Dec. 7, 1993

[51] Int. Cl.⁶ ............................................. A61M 29/00
[52] U.S. Cl. ......................................... 604/96; 604/101
[58] Field of Search ................................. 604/96–103, 604/265, 266, 52, 53; 606/192–196

[56] References Cited

U.S. PATENT DOCUMENTS

| | | |
|---|---|---|
| 550,238 | 11/1895 | Allen, Jr. . |
| 2,175,726 | 10/1939 | Gebauer . |
| 2,642,874 | 6/1953 | Keeling . |
| 3,948,254 | 4/1976 | Zaffaroni . |
| 3,977,408 | 8/1976 | MacKew . |
| 4,299,226 | 11/1981 | Banka . |
| 4,423,725 | 1/1984 | Baran et al. . |
| 4,445,892 | 5/1984 | Hussein et al. . |
| 4,496,345 | 1/1985 | Hasson . |
| 4,501,580 | 2/1985 | Glassman . |
| 4,531,936 | 7/1985 | Gordon . |
| 4,581,017 | 4/1986 | Sabota . |
| 4,627,837 | 12/1986 | Gonzalo . |
| 4,655,746 | 4/1987 | Daniels et al. . |
| 4,693,243 | 9/1987 | Buras . |
| 4,705,502 | 11/1987 | Patel . |
| 4,723,556 | 2/1988 | Sussman . |
| 4,781,677 | 11/1988 | Wilcox . |
| 4,821,714 | 4/1989 | Smelser . |
| 4,824,436 | 4/1989 | Wolinsky . |
| 4,832,688 | 5/1989 | Sagae et al. . |
| 4,883,459 | 11/1989 | Calderon . |
| 4,973,305 | 11/1990 | Goltzer . |
| 4,976,692 | 12/1990 | Atad . |
| 4,994,033 | 2/1991 | Shockey et al. . |
| 5,049,132 | 9/1991 | Shaffer et al. . |
| 5,087,244 | 2/1992 | Wolinsky et al. . |
| 5,090,960 | 2/1992 | Don Michael . |
| 5,092,841 | 3/1992 | Spears . |
| 5,098,381 | 3/1992 | Schneider . |
| 5,102,402 | 4/1992 | Dror et al. . |
| 5,112,305 | 5/1992 | Barath et al. . |
| 5,135,484 | 8/1992 | Wright . |
| 5,163,905 | 11/1992 | Don Michael . |
| 5,176,638 | 1/1993 | Don Michael . |
| 5,180,366 | 1/1993 | Woods . |
| 5,199,951 | 4/1993 | Spears . |
| 5,213,576 | 5/1993 | Abiuso et al. . |
| 5,236,413 | 8/1993 | Feiring . |
| 5,236,424 | 8/1993 | Imran . |
| 5,250,070 | 10/1993 | Parodi . |
| 5,318,531 | 6/1994 | Leone ........................... 604/101 X |
| 5,324,261 | 6/1994 | Amundson et al. .................. 604/96 |

FOREIGN PATENT DOCUMENTS

| | | |
|---|---|---|
| 9211895 | 7/1992 | WIPO . |
| 9211896 | 7/1992 | WIPO . |
| 9308864 | 5/1993 | WIPO . |

*Primary Examiner*—John D. Yasko
*Attorney, Agent, or Firm*—Haugen and Nikolai

[57] ABSTRACT

An intravascular material delivery dilation catheter having a pair of longitudinally spaced inflatable balloons with a drug delivery region defined therebetween. The catheter is ideally suited for use after a PTCA procedure, wherein the proximate balloon seals the blood vessel while the distal balloon is uniquely contoured when inflated to define fluid communication paths therepast and proximate a blood vessel to be treated. The distal balloon, when inflated, has four lobes but could also be textured. Each lobe is separated from the next by a groove, which groove in combination with the blood vessel inner wall forms a fluid communication path therebetween. Upon inflation of both balloons in a blood vessel, a medicament such as heparin can be injected, via the drug delivery region between the inflated balloons, wherein the medicament flows past the distal balloon at a selected rate. Accordingly, a medicament can be injected directly to a treatment site rather than injected as a bolus dose, thus, a smaller dosage may be employed to minimize side effects. Alternatively, perfusion can be accomplished by only partially inflating the proximate balloon to constrict flow therepast, or eliminating the proximate balloon entirely, where the drug delivery region is disposed upstream of the contoured distal balloon.

34 Claims, 4 Drawing Sheets

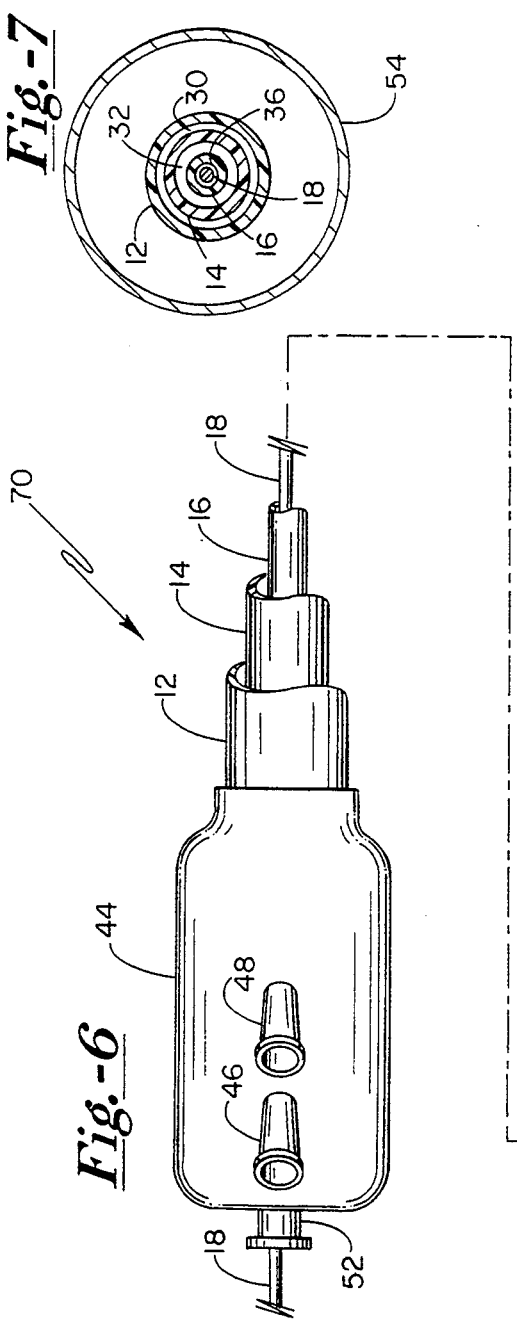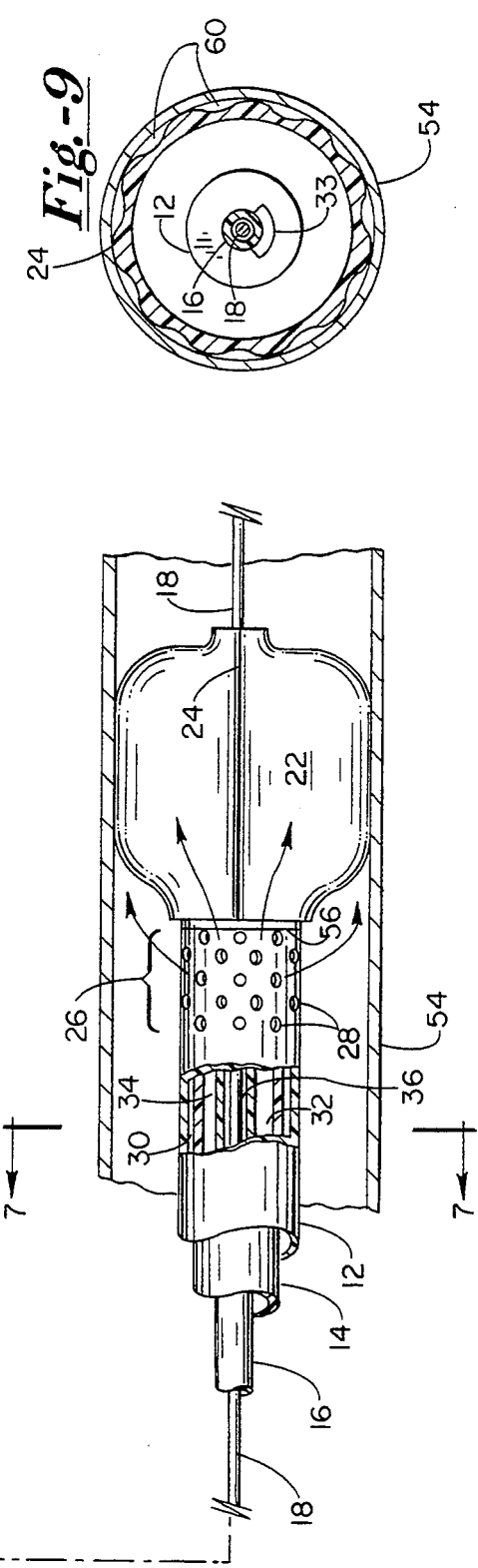

DRUG DELIVERY PTCA CATHETER AND METHOD FOR DRUG DELIVERY

BACKGROUND OF THE INVENTION

I. Field of the Invention

This invention relates generally to an apparatus and method for delivering a drug to a patient's vascular system after performing a percutaneous transluminal coronary angioplasty (PTCA) procedure, and more particularly to an improved catheter arrangement which facilitates delivering and concentrating a drug to a treatment site in a blood vessel.

II. Discussion of the Prior Art

A percutaneous transluminal coronary angioplasty (PTCA) procedure typically consists of introducing a catheter with a single inflatable balloon into a patient's vascular system and positioning the balloon proximate a stenotic lesion to be treated. With the balloon juxtaposed relative to the blockage or constriction, an inflation fluid is introduced through a lumen of the catheter and made to inflate the balloon to expand the balloon against the blockage and to spread or open the obstructed blood vessel. This catheter is then removed and a second catheter is introduced into the vascular system. Subsequently, a medicament is introduced through the second catheter and to the site to treat the stenotic lesion to inhibit platelet aggregation at the site. This procedure is widely used in modern medicine and is far less traumatic than prior coronary bypass surgical procedures.

Certain drugs have been found to be more effective than others in reducing restenosis. These drugs help reduce the necessity of repeating the PTCA procedure. For instance, there are drugs which show a tendency to inhibit smooth muscle cell growth. Because these drugs can have undesirable side effects, it is not desirable that they be injected as a bolus dose into a peripheral vein and merely allowed to be carried by the blood stream to the situs of the stenotic lesion. However, and in accordance with the present invention, if that drug can be administered directly to the lesion, a significantly smaller dose may be employed and the side effects minimized.

Heparin is one such known drug for inhibiting clotting which can be delivered by injection as a bolus but which is known to have disadvantages. For instance, some patients, such as ulcer patients or patients with high blood pressure, are contraindicated for the administration of such large amounts of heparin. Other drugs, such as aspirin or persantin, are effective in inhibiting platelet aggregation at a treated site and thus to inhibit restenosis. Anti-coagulation medications and medications adapted to treat damaged arteries and to dissolve thrombus, are also preferably dispensed after the PTCA procedure.

One particular intravascular drug delivery dilation catheter ideally suited for a PTCA procedure is that disclosed in U.S. Pat. No. 4,994,033 which is assigned to the assignee of the present invention, the teachings of which are incorporated herein by reference. This particular catheter comprises concentrically arranged flexible plastic expander members with a space defined between the walls thereof for receiving a liquid medicament. A plurality of minute holes are formed through the outer expander member. When both expander members inflate, the drug is caused to be ejected out the tiny pores of the outermost expander member and against the adjacent tissue of the blood vessel. Using this device, a significantly smaller dosage may be employed to directly treat a stenotic lesion. This reduces the side effects of the particular medicament. During application of the medicament, the outer expander member is in direct contact with and seals against the blood vessel inner wall to restrict perfusion of blood through the interface. Thus, the medicament is not easily distributed throughout the entire body.

A balloon catheter for delivering therapeutic agents is disclosed in U.S. Pat. No. 5,049,132. This balloon catheter comprises a first balloon encompassed by a second balloon, the second balloon having a plurality of apertures defined therethrough for locally applying a medicament, such as heparin, to a stenotic lesion or a damaged coronary artery. This inflatable outer balloon is also adapted to seal against a blood vessel inner wall for a short time while the medicament is applied thereto. This device uses the medication as the balloon inflation fluid. The medication is administered in a volume and at a pre-determined pressure so that the balloon is expanded at a desired rate despite the leakage of medication through the apertures in the balloon wall.

Both of these prior art PTCA drug delivery catheters comprise two concentric balloons rather than a pair of balloons longitudinally spaced from one another along the catheter shaft. The drug delivery region in each device is defined through the outer wall of the outermost balloon, and thus, is positioned against the blood vessel wall in close conformity therewith. Both of these devices are adapted to allow medication to be slowly absorbed through a blood vessel wall proximate the balloon, and are not adapted to flush a large dose of a medicament past a treatment site to bathe the site.

OBJECTS

It is accordingly a principle object of the present invention to provide an improved dilation catheter suitable for injecting a variety of drugs directly to a treatment site, and an improved method for delivering the drugs.

It is also a principle object of the present invention to provide an improved dilation catheter suitable for injecting a drug during the course of or after a PTCA procedure.

Another object of the invention is to provide a dilation catheter which permits administration of a liquid medicament or other suitable substance directly to the lesion being treated so as to inhibit restenosis.

Yet a further object of the present invention is to provide a dilation catheter suitable for use in or after a PTCA procedure and which restricts blood flow in the blood vessel while a medicament is effectively applied to the site of a stenotic lesion.

Another object of the present invention is to provide a catheter suitable for performing perfusion.

Still yet a further object of the present invention is to provide a method for delivering a drug directly to a stenotic lesion.

SUMMARY OF THE INVENTION

The foregoing objects and advantages of the present invention are achieved by providing an intravascular, drug-delivery, dilation catheter having a pair of longitudinally spaced inflatable expander members (balloons) with a drug delivery region defined therebetween. The second and most distal balloon has a contoured outer surface when inflated and which defines a plurality of fluid passages between the periphery of the second balloon and the inner wall of the blood vessel being treated. Thus, a medicament can be dispensed into the void between the inflated balloons and allowed to flow slowly past the tissue of the blood vessel wall adjacent the inflated second balloon to effectively bathe the treated site with the medicament. The first balloon is inflated to totally seal the blood vessel proximal and upstream of the treatment site, while the second balloon is inflated to constrict flow in the blood vessel to allow leakage of medication therepast and adjacent the blood vessel wall. If desired, the inflated second balloon could be expanded to spread the blood vessel as the medicament flows therepast. An aspiration port is in communication with the drug delivery region such that the void defined between the pair of inflated balloons can be flushed and aspirated before and after dispensing the medicament to increase the drug effectiveness, such as during or after the PTCA procedure.

In the preferred embodiment, the second balloon has a plurality of lobes when inflated such that a fluid path is defined between each pair of adjacent lobes. With four lobes, four longitudinal fluid paths are created in cooperation with the blood vessel's inner wall, each channel extending along the groove between the defined lobes. However, other designs can be implemented as well wherein a portion of the second inflatable balloon engages the blood vessel wall while another portion is spaced from the blood vessel wall to define one or more channels therebetween. Of course, the contours of the second balloon can be designed such that either large or small, few or many, straight, curved or spiraled fluid paths result when the second balloon is inflated. The channels are created by selectively choosing the thickness of the second balloon walls, the walls being thinner proximate the crowns of the lobes than proximate the valleys such that the lobes tend to stretch more than the valleys when the balloon in inflated. Alternatively, the second balloon can have walls of uniform thickness, wherein the outer surface is textured and has a rough surface, or includes a plurality of outwardly-extending spaced protrusions.

In an alternative preferred embodiment, the first or proximal balloon can also be contoured when inflated, only partially inflated, or eliminated altogether to provide perfusion. Thus, a medicament can be effectively mixed with a small flow of blood and together allowed to flow slowly past a selected portion of the blood vessel. Accordingly, a single balloon catheter can provide effective localized drug treatment as well.

BRIEF DESCRIPTION OF THE DRAWINGS

FIG. 6 is a greatly enlarged, partially sectioned view of a single-balloon intravascular drug delivery catheter disposed in a blood vessel in accordance with an alternative preferred embodiment of the invention suitable for perfusion;

FIG. 7 is a cross-sectional view taken at 7—7 in FIG. 6 illustrating the several lumens extending through the catheter;

FIG. 8 is a sectional view 4—4 taken in FIG. 1 where the distal balloon has a textured outer surface; and FIG. 9 is a sectional view 4—4 taken in FIG. 1 where the distal balloon is comprised of a plurality of outwardly-extending protrusions.

Other objects, features and advantages of the present invention will become apparent to those skilled in the art through the Description of the Preferred Embodiment, Claims, and drawings herein wherein like numerals refer to like elements.

DESCRIPTION OF THE PREFERRED EMBODIMENT

Figure 1:
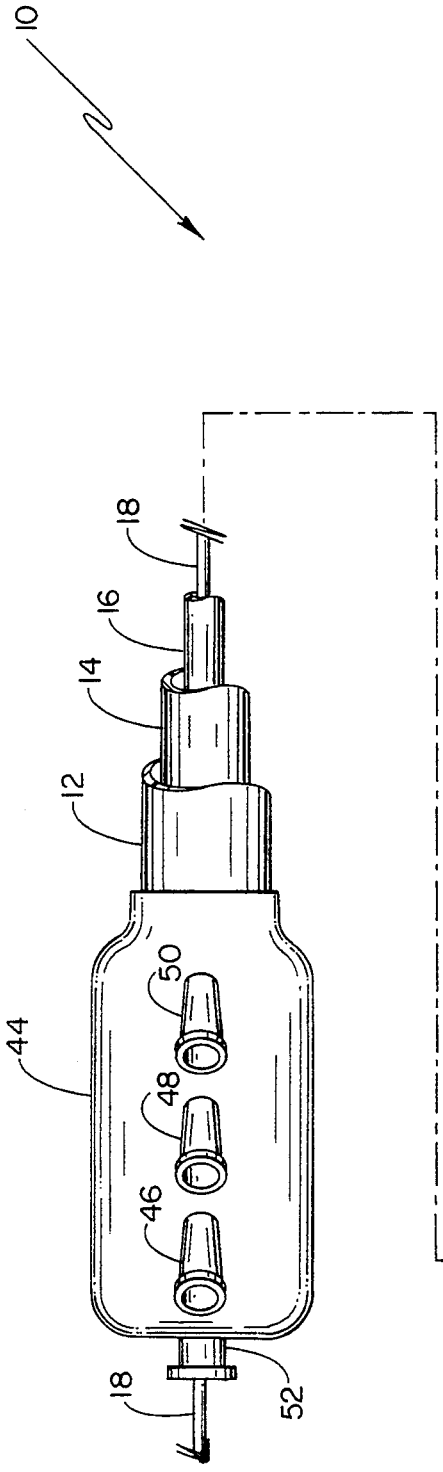
FIG. 1 is a greatly enlarged, partially sectioned two-balloon intravascular drug delivery catheter disposed in a blood vessel in accordance with a preferred embodiment of the present invention.
Figure 1:
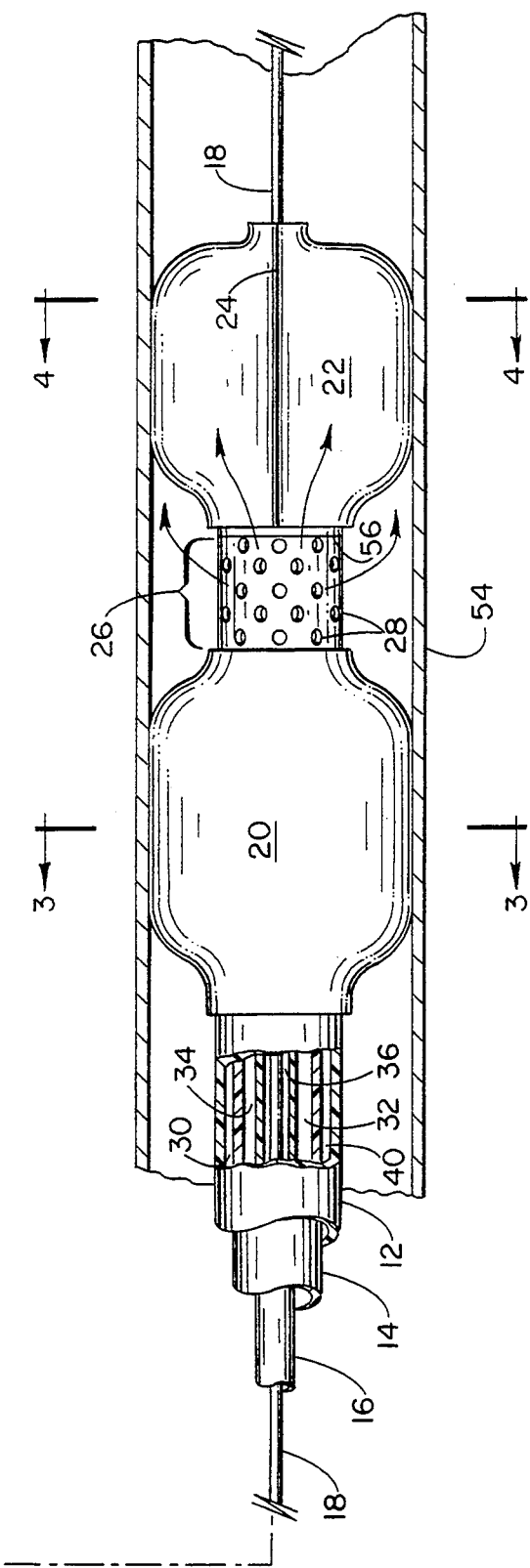
Figure 2:
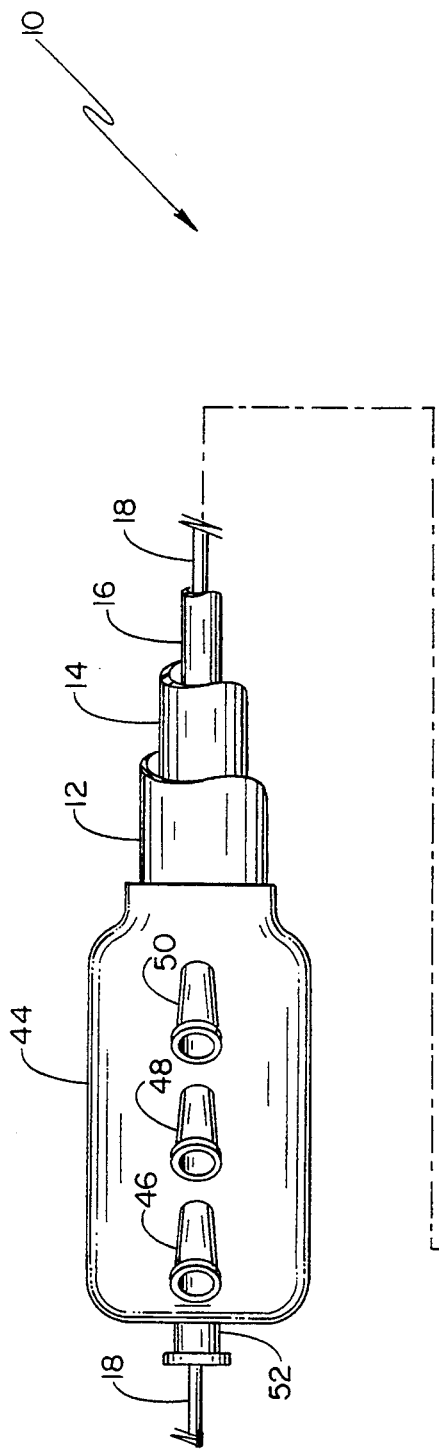
FIG. 2 is a greatly enlarged, partially sectioned view of the catheter illustrating the various lumens, balloons, and drug delivery region.
Figure 2:
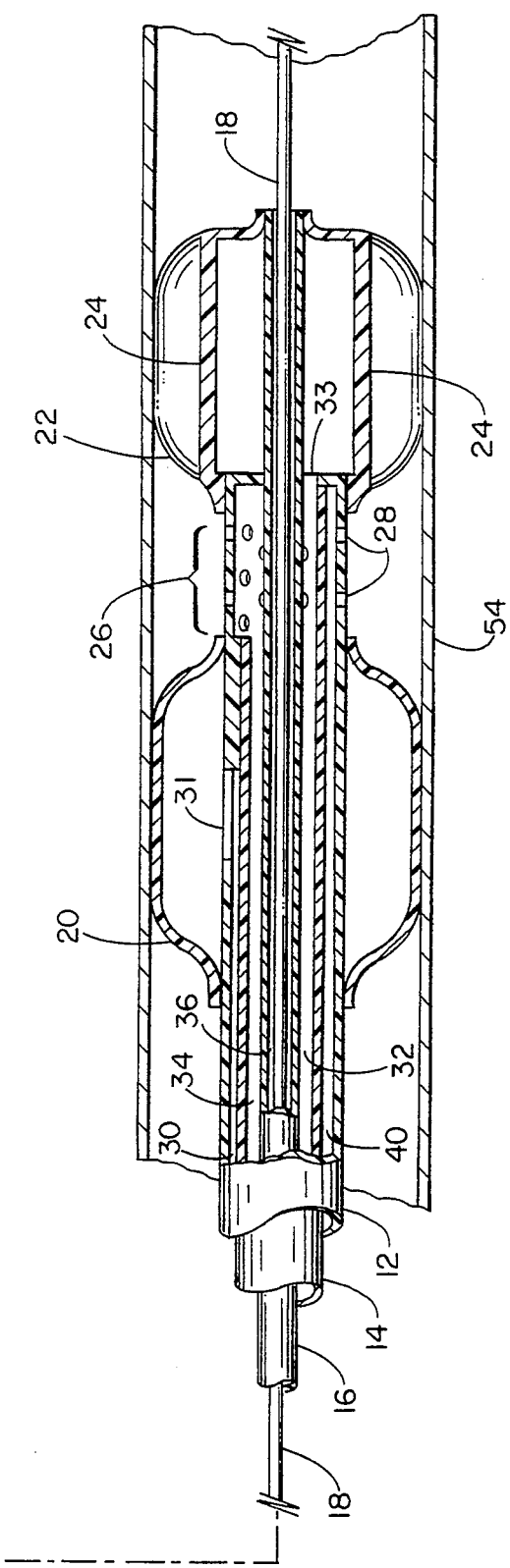

Referring now to FIGS. 1 and 2, an intravascular drug-delivery dilation catheter comprising a preferred embodiment of the present invention is generally shown at 10. It is seen to include first, second and third concentrically or coaxially disposed elongated flexible plastic tubular members identified by numerals 12, 14 and 16, respectively. The three tubes may typically be approximately 135 cms. in length and the outermost tube 12 dimensioned to readily pass through the portion of the vascular system proximal of the treatment site. The arrangement is depicted as an over-the-wire system in that it may be made to pass over an elongated guidewire 18 once that guidewire has been routed through a guide catheter (not shown) with the distal end of the guidewire passing through the site of the lesion or treatment site and beyond.

At the distal end of outermost tube 12 is a pair of inflatable balloons shown as a proximal balloon 20 and a distal balloon 22. As is illustrated, proximal balloon 20 is generally elongated and cylindrical in shape when inflated. Distal balloon 22 is particularly characterized as being non-circular and contoured when inflated such that a plurality of equidistant radially extending lobes are defined. Alternatively, the distal balloon's contour can be textured and have a rough surface (FIG. 8), or comprise a plurality of outwardly extending protrusions (FIG. 9). Two balloons may be fabricated from PET as non-distensible plastic members, or from silicone, nylon, or polyethylene as distensible plastic members, each appropriately bonded to the catheter body 12 as shown. The lobes are created by controlling the thickness of the balloon wall when manufactured (See FIG. 4). Specifically, the walls are more elastic and thin at some portions to define the crowns of the lobes when inflated, and relatively thicker at other sections and which stretch less when inflated to define valleys. Alternatively, the degree of distensibility of the balloon in different zones can be varied by appropriately irradiating the plastic material to affect the degree of cross-linking of the molecules. When inflated, a longitudinal groove 24 is defined between adjacent lobes which serves as a fluid path along distal balloon 22 when it is inflated within a blood vessel (see FIG. 4). Alternatively, the balloon 22 can be textured when inflated to allow fluid flow therepast, as shown in FIG. 8, or comprise a plurality of outwardly extending protrusions spaced from one another to define a fluid path therepast, as shown in FIG. 9.

A drug delivery region 26 is formed along outermost tube 12 between proximal balloon 20 and distal balloon 22, the tube 12 in this region including a plurality of pores or apertures 28 for dispensing medication and/or aspirating fluid present between the inflated balloons once the catheter has been inserted in a blood vessel. As can be seen from the partially broken-away and sectioned portion of FIGS. 1 and 2, a first lumen 30 is in fluid communication with the interior of proximal balloon 20 at opening 31. A second lumen 32 extends the length of tubular member 12 and is in fluid communication with distal balloon 22 at opening 33 and terminates thereat. A third lumen 34, also extending the full length of the tubular member 12 is in fluid communication with drug delivery region 26 and consequently apertures 28. A further lumen 36 extends through the center of tube 16 and slidably receives guidewire 18 as shown.

Figure 3:
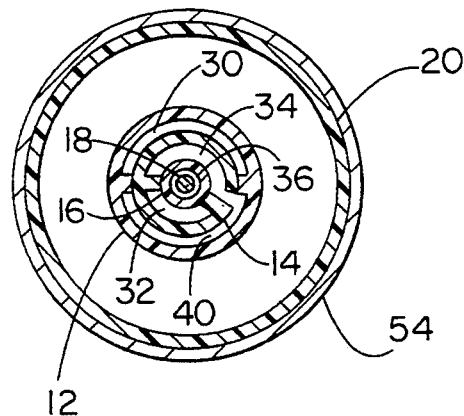
FIG. 3 is a cross-sectional view 3—3 taken in FIG. 1 of the proximal balloon illustrating the several lumens extending through the catheter.
Figure 5:
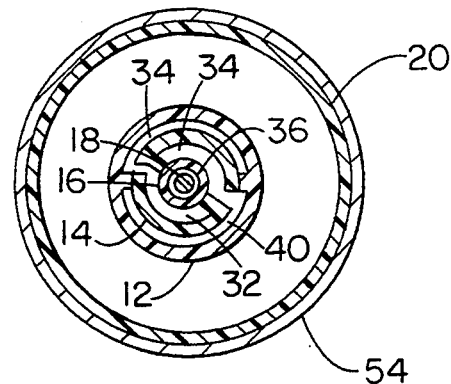
FIG. 5 is a cross-sectional view taken at 3—3 in FIG. 1 where inflation lumens 30 and 32 are in fluid communication with each other.

First and second inflation lumens 30 and 32 are isolated from one another, as shown in FIG. 3, such that both proximal balloon 20 and distal balloon 22 can be independently inflated by introducing an inflation fluid through ports on the catheter hub 44. However, it is to be recognized that balloon inflation lumens 30 and 32 could be in fluid communication with one another, as shown in FIG. 5, such that both balloons 20 and 22 will be simultaneously inflated by a single fluid source. An additional lumen 40 is provided in fluid communication with lumen 34 for aspirating fluid from perfusion region 26. However, lumens 34 and 40 could be isolated from one another as well, with lumen 40 accessible from a dedicated port at the handle such that fluid can be separately injected and/or aspirated via both lumens.

Suitably attached to the proximal end of the catheter assembly is a molded plastic hub 44 having a trio of ports 46, 48 and 50, individually communicating with the lumens 30, 32 and 34. The ports 46, 48 and 50 may be Luer fittings for facilitating the attachment of an inflation tool such as a syringe of the type shown in the Goodin et al. U.S. Pat. No. No. 4,723,938, which is assigned to the assignee of the present invention.

Disposed on the proximal end of the hub 44 is a stub 52 having a bore which joins to the lumen 36 of the innermost tube 16 for accommodating the guidewire 18. When the guidewire is removed, the lumen 36 of the innermost tube may be utilized to perfuse blood distally of the treatment site to inhibit ischemia downstream or to introduce a contrast media. Alternatively, the lumen 36 can be used as a way of measuring pressure at the treatment site.

The concentric catheter bodies 12, 14 and 16 may be made from a variety of materials now commonly used in fabricating angioplasty and angiographic catheters. Typical materials are PVC, nylon and polyurethane. The guidewire 18 may be fabricated from stainless steel also in accordance with techniques well known in the patent literature.

Referring to FIG. 1, in use, the guidewire 18 would conventionally be routed through an introducer or guide catheter (not shown) and across the lesion or site to be treated in blood vessel 54. Following that, the distal end of the innermost tube 16 is fitted over the proximal end of the guidewire and then advanced along the guidewire until the lobed distal balloon 22 is juxtaposed proximate the site to be treated. The proximate balloon 20 will then be positioned upstream (proximal) thereof. FIG. 1 shows proximal balloon 20 and distal balloon 22 in their inflated configuration within blood vessel 54, it being understood that during the routing operation, those balloons would be deflated and tightly wrapped to conform to the exterior of tubular member 12.

Figure 4:
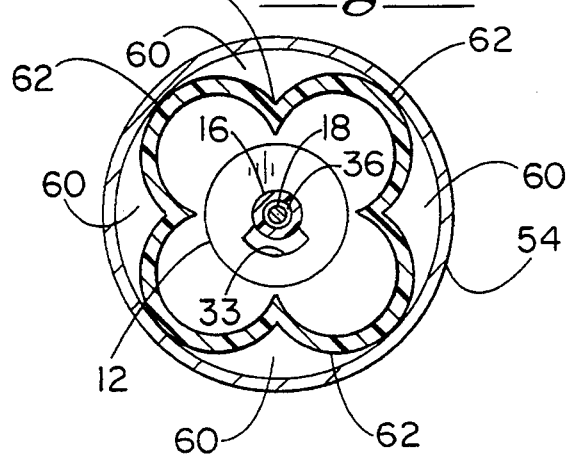
FIG. 4 is a cross-sectional view 4—4 taken in FIG. 1 of the inflated contoured distal balloon in a coronary artery and defining a plurality of fluid channels.

Once the distal end of catheter 10 is appropriately positioned with the aid of a radiopaque marker band 56, an inflation fluid is next injected through proximal port 46 and thus through lumen 30 to fully inflate proximal balloon 20, thus sealing the blood vessel such as a coronary artery. However, if perfusion is desired, first balloon 20 can be only partially inflated to float in the blood vessel and constrict flow, comprised of a contoured balloon when inflated like distal balloon 22, or eliminated altogether as will be discussed shortly in reference to FIG. 6. Next, an inflation fluid will be injected through port 48 and thus through lumen 32 and into the interior of lobed distal balloon 22 until this balloon is at least partially inflated and disposed proximate the vessel wall to constrict flow therethrough, and may or may not engage the blood vessel inner wall. Preferably, the distal balloon 22 is fully inflated and engages the blood vessel wall at the site of the lesion to engage the lesion (see FIGS. 4, 8 and 9). Once inflated, a plurality of fluid paths or channels 60 are defined by the valleys of the lobed configuration, one between each lobe valley 62 and the blood vessel wall 64 as shown in FIG. 4.

When inflated, the crown of each lobe 62 engages and seals with the inner proximal wall of blood vessel 54. However, the plurality of fluid paths 60 remain open to allow fluid communication across the balloon's surface, as shown in FIGS. 1 and 4. Next, a selected dispersant, such as heparin or other suitable drug containing liquid for inhibiting formation of a thrombus, or aspirin or persantin for inhibiting platelet aggregation at the treatment site, is introduced through the distal Luer port 50 and through lumen 34 to the confines of drug delivery region 26 and thus dispensed through apertures 28 into the void defined between inflated balloons 20 and 22. Once this void is filled with medication, additional injection of medication into the void causes the medication to be swept past inflated distal balloon 22 at a corresponding and controllable rate through the fluid channels 60 defined by longitudinally extending grooves 24 and the blood vessel inner wall, and in intimate contact with the treatment site, as shown in FIG. 1 by the arrows illustrating flow patterns. The first inflated balloon seals the blood vessel 54 upstream from the treatment site such that the drug does not wash away too quickly past the drug treatment site, and further ensures that only the medication will flow past the drug treatment site.

By selecting an appropriate depth of grooves 24 between adjacent lobes 62, the rate at which this dispensed medication flows past expanded distal lobe 22 can be selected. Accordingly, the shallower the groove 24, the slower rate at which medication is pushed therepast. Similarly, the number of grooves 24 defined can also be chosen to control the rate at which medication flows therepast. For instance, distal balloon 22 can be designed to have only a pair of lobes (when inflated) and a corresponding pair of grooves 24 for accommodating fluid flow. If desired, the longitudinally extending grooves 24 can be non-linear, curved, or spiraled rather than linear to selectively alter the rate and pattern at which medicament flows therepast. Alternatively, the distal balloon 22 can be textured and have a rough surface when inflated (see FIG. 8) or include a plurality of lobes or protrusions (see FIG. 9) so that the balloon 22 only partially seals blood vessel 54 when inflated, thus allowing medication to flow slowly therepast.

Accordingly, one key feature of the present invention is that distal balloon 22 is uniquely contoured when inflated to seal against a portion of a blood vessel 54 at one portion, but which remains spaced from the blood vessel wall at other grooved portions thereof to allow leakage and communication of a dispensed medicament therepast proximate a treatment site. However, the distal balloon 22 can also be only partially inflated and disposed proximate the vessel inner wall but spaced therefrom, in a floating arrangement, to constrict flow of medication therepast. The contour of the inflated distal balloon 22 is defined when inflated by proper attention to wall thickness at time of manufacture, as shown in FIG. 4. Alternatively, the wall can have a uniform thickness but which has a textured exterior surface (FIG. 8), or which includes a plurality of outwardly extending spaced protrusions (FIG. 9). Radiopaque marker 56 can be used to locate distal balloon 22 adjacent or slightly upstream from a site to be treated.

Prior to injection of a medicament, the apertures of drug delivery region 26 can be used in combination with lumen 34 and/or 40 to flood and flush the void between the inflated balloons and to aspirate this and other fluids which may be disposed therebetween. Thus, when a medicament is subsequently injected via the drug delivery region 26 into this void, the medicament will not be diluted and thus can be concentrated against and bathe the blood vessel wall to be treated. Flushing fluids, such as saline, are commonly used. Thus, the blood vessel wall can then be doped with the medicament effectively.

After the PTCA procedure, the blood vessel wall, such as a coronary artery, can be only occluded for a short period of time, e.g. one minute. During this time, anticoagulation drugs or drugs created to dissolve clots can be injected using the present apparatus and method. The combination of the pair of longitudinally spaced balloons with a drug delivery region defined therebetween, wherein the distal balloon is contoured when inflated, has been found to be effective in providing a long-term patency to the treated blood vessel or the coronary artery. The size and shapes of fluid paths 60 can be custom designed through appropriately designed lobes 62 and channels 24 so that they are not easily plugged, and so that the fluid flow rate of the medicament flowing therepast can be particularly chosen. Thus, one key feature of the present invention is that the rate at which medicament can flow past a treatment site can be chosen by using a particularly designed distal balloon 22. While purely exemplary, drugs may include aspirin or a persantin for inhibiting platelet aggregation at the site, heparin or prostaglandin for inhibiting clotting, or other drugs found to be effective in inhibiting smooth muscle cell growth.

While an inflatable proximal balloon 20 is ideal for sealing a blood vessel before dispensing a medicament via drug delivery region 26, it needs to be recognized that limitation to an inflatable balloon is not to be inferred for other devices and methods for sealing or constricting a blood vessel upstream from drug delivery region 26 can be used as well. Thus, the particular method of the present invention encompasses first sealing a blood vessel upstream from a chosen blood vessel site, such as the locus of a stenotic lesion, in the course of or after a PTCA, inflating a custom designed balloon or flow impeding member at or downstream from this site, and then injecting a medicament between the proximal balloon (sealing means) and the distal contoured balloon, such that the medicament flows past the contoured distal balloon and adjacent the site to be treated.

While four lobes, such as a clover design, is the contour of the preferred embodiment, it is also to be recognized that different contours such as outwardly-extending protrusions or textures, equivalent in function to rounded lobes, as shown, are suitable for the present invention as well. The resulting recesses, in combination with the blood vessel inner wall when the contoured balloon is inflated, form a fluid path such that medicament can leak therepast at a controlled rate. Accordingly, limitations to the particular design of the fluid path is not to be inferred. Further yet, the amount of inflation fluid injected into distal balloon 22 can be selectively controlled as well, via port 48, such that this balloon can be selectively and controllably inflated to selectively control the cross section opening of paths 60 as well. Thus, the rate at which medicament flows past distal balloon 22 proximate the treatment site can be selectively controlled using a single apparatus, such as the distal balloon 22 shown in FIG. 1.

In an alternative preferred embodiment of the present invention as shown at 70 in FIG. 6, perfusion can be performed by the present invention as well. By only partially inflating proximal balloon 20, providing an inflated proximal balloon which is contoured, such as one identical to balloon 22 in FIG. 1 or which is textured (FIG. 8), or providing a proximal balloon 20 including outwardly-extending protrusions (FIG. 9), or eliminating proximal balloon 20 altogether as shown in FIG. 6, perfusion is possible and will now be discussed.

The single-balloon catheter 70 in FIG. 6 is very similar to the two-balloon catheter shown in FIG. 1 with the exception that only a single contoured distal balloon 22 is provided with drug delivery region 26 being defined proximal and upstream therefrom. Correspondingly, a reduced number of lumens and ports are required for operation of this catheter. Specifically, a first lumen 30 is provided which communicates medicament from port 46 to drug delivery region 26 and pores 28, and a second lumen 32 which extends from port 48 to and terminates at distal balloon 22 for inflation thereof as previously described with regards to the catheter 10 of FIG. 1. Lumen 36 is provided for receiving guidewire 18 as shown in FIG. 7.

To allow perfusion, restricted and reduced blood flow is permitted through fluid passageways 60 while medicament is injected upstream of inflated distal balloon 22 via drug delivery region 26 and thus mixes therewith. Both the blood and medicament will together be slowly swept past inflated contoured distal balloon 22 and in close proximity with the blood vessel inner wall to bathe the site, such as during or after a PTCA procedure. For instance, distal balloon 22 can be inflated to expand the blood vessel to reduce stenosis as medicament is being swept therepast, or implemented after a PTCA procedure is performed by a previously introduced catheter. Any of the embodiments shown for distal balloon 22, such as the lobed balloon (FIG. 1), a textured balloon (FIG. 8), or a balloon including protrusions (FIG. 9) are suitable and can be implemented as desired by the physician.

In summary, limitation to the particular contours of contoured distal balloon 22, or limitation to implementing proximal balloon 20 in a partially or totally inflated configuration, is not to be inferred. Rather, providing a distal contoured balloon 22 when inflated with a drug delivery region disposed proximate and upstream thereof is one of the primary features of the present invention. The proximal balloon 20 can be eliminated altogether or left uninflated if desired. Further, the present invention can be implemented during or after a PTCA procedure, and may incorporate perfusion if desired.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

I claim:

1. An intravascular drug delivery dilatation catheter comprising:
   an elongated, flexible, tubular catheter shaft having a proximal end and a distal end with a first, second and third lumen each extending therealong, said shaft having first and second inflatable balloons longitudinally spaced from one another proximate said distal end and with a drug delivery region disposed between said first and second balloons, said first and second lumens being in fluid communication with said first and second balloons, respectively, and said third lumen being in fluid communication with said drug delivery region, said second balloon when inflated having an outer contoured surface for creating a fluid flow path from said drug delivery region and along said second balloon outer surface when said second balloon is inflated in a patient's blood vessel.

2. The drug delivery dilation catheter as specified in claim 1 wherein said second balloon comprises a plurality of lobes when inflated, there being a longitudinal fluid path between each pair of adjacent ones of said lobes.

3. The drug delivery dilation catheter as specified in claim 2 wherein said second balloon has a balloon wall of a varying thickness to define said lobes when inflated.

4. The drug delivery dilation catheter as specified in claim 2 wherein said fluid paths are located angularly equidistantly from one another to facilitate uniform passage of a medication dispensed from said drug delivery region along said outer surface of said second balloon.

5. The drug delivery catheter as specified in claim 1 wherein said second balloon outer surface is textured when inflated for creating said fluid flow path.

6. The drug delivery catheter as specified in claim 1 wherein said second balloon outer surface includes a plurality of outwardly extending protrusions when inflated.

7. The drug delivery catheter as specified in claim 1 wherein said second balloon is comprised of a distensible material.

8. The drug delivery catheter as specified in claim 1 wherein said second balloon is comprised of a nondistensible material.

9. The drug delivery dilation catheter as specified in claim 1 wherein said first and second lumen are in fluid communication with each other to facilitate simultaneous inflation of said first and second balloons.

10. The drug delivery dilation catheter as specified in claim 1 further including a fourth lumen extending therethrough from said proximal end to said distal end for receiving a guidewire therethrough.

11. An intravascular drug delivery catheter, comprising:
    an elongated, flexible, tubular catheter shaft having a proximal end and a distal end with a first and second lumen extending therealong, said shaft having an inflatable balloon disposed at the distal end thereof and with a drug delivery region disposed between said proximal end and said balloon, said first lumen being in fluid communication with said balloon and said second lumen being in communication with said drug delivery region, said balloon when inflated having an outer contoured surface for creating a fluid flow path from said drug delivery region and along said balloon outer surface when said balloon is inflated in a patient's blood vessel.

12. The drug delivery dilation catheter as specified in claim 11 wherein said balloon comprises a plurality of lobes when inflated, there being a longitudinal fluid path between each pair of adjacent ones of said lobes.

13. The drug delivery dilation catheter as specified in claim 12 wherein said balloon has a balloon wall of a varying thickness to define said lobes when inflated.

14. The drug delivery dilation catheter as specified in claim 12 wherein said fluid paths are located angularly equidistantly from one another to facilitate uniform passage of a medication dispensed from said drug delivery region along said outer surface of said balloon.

15. The drug delivery catheter as specified in claim 11 wherein said balloon outer surface is textured when inflated for creating said fluid flow path.

16. The drug delivery catheter as specified in claim 11 wherein said balloon outer surface includes a plurality of outwardly extending protrusions when inflated.

17. The drug delivery catheter as specified in claim 11 wherein said balloon is comprised of a distensible material.

18. The drug delivery catheter as specified in claim 11 wherein said balloon is comprised of a nondistensible material.

19. The drug delivery dilation catheter as specified in claim 11 further including a fourth lumen extending therethrough from said proximal end to said distal end for receiving a guidewire therethrough.

20. The drug delivery dilation catheter as specified in claim 11 wherein said drug delivery region is disposed proximate said balloon.

21. A method of delivering a dispersant into a selected portion of a patient's blood vessel comprising steps of:
    (a) providing an elongated, flexible catheter having first and second inflatable balloons longitudinally spaced from one another proximate a distal end of said catheter with a drug delivery region disposed between said first and second balloons;
    (b) inserting said catheter into the patient's blood vessel such that said second balloon is disposed adjacent an inner wall of said blood vessel along said selected portion thereof;

(c) inflating said first balloon to seal against the blood vessel inner wall;

(d) inflating said second balloon such that a first portion thereof is disposed closely proximate but spaced from said blood vessel's inner wall;

(e) injecting said dispersant through said drug delivery region into the blood vessel between said first and second balloon such that the dispersant flows between and past said inflated second balloon and said blood vessel inner wall.

22. The method as specified in claim 21 wherein said second balloon is contoured when expanded causing said first portion of said second balloon to be spaced from said blood vessel inner wall while a second portion of said second balloon engages the blood vessel inner wall, whereby at least one drug flow path is defined between said blood vessel inner wall and said first portion of said inflated second balloon.

23. The method as specified in claim 22 comprising the step of injecting a drug-containing liquid as said dispersant.

24. The method as specified in claim 21 wherein said second balloon is positioned proximate an atherosclerotic lesion in step (b).

25. A method of delivering a dispersant into a selected portion of a patient's blood vessel, comprising the steps of:

(a) providing a catheter having a first and second longitudinally spaced flow impeding members with a drug delivery region defined therebetween;

(b) disposing said catheter in said patient's blood vessel such that said first flow impeding member is positioned upstream of said blood vessel selected portion and said second flow impeding member is positioned downstream thereof and closely proximate said blood vessel selected portion;

(c) impeding flow in said blood vessel at said first flow impeding member, and impeding flow in said blood vessel at said second flow impeding member such that a fluid can flow past said second flow impeding member and adjacent the blood vessel selected portion; and (d) dispensing a dispersant from the catheter drug delivery region such that said dispersant flows past said second flow impeding member and closely proximate said blood vessel selected portion.

26. The method as specified in claim 25 wherein said first flow impeding member seals said blood vessel in step (c) to prevent flow therepast.

27. The method as specified in claim 25 wherein said second flow impeding member is an inflatable balloon with a contoured outer surface when inflated, and step (c) includes the step of disposing said contoured outer surface proximate said blood vessel selected portion to constrict flow therepast.

28. The method as specified in claim 27 wherein said first flow impeding member is an inflatable balloon, and is inflated in step (c) to impede flow in said blood vessel.

29. The method as specified in claim 28 wherein said second flow impeding member is positioned in step (b) proximate an atherosclerotic lesion.

30. The method as specified in claim 25 comprising the step of injecting a drug containing liquid as said dispersant.

31. The method as specified in claim 25 including the step of introducing a guidewire through the patient's blood vessel to the blood vessel selected portion prior to introducing said catheter, and subsequently positioning said catheter over said guidewire and through the patient's blood vessel.

32. A method of delivering a dispersant into a selected portion of a patient's blood vessel, comprising the steps of:

(a) providing a catheter having a proximate end and a distal end, a first flow impeding member at said distal end, and a drug delivery region disposed between said catheter proximate end and said flow impeding member;

(b) disposing said catheter in said patient's blood vessel such that said flow impeding member is positioned proximate said blood vessel selected portion and said drug delivery region is positioned upstream thereof;

(c) impeding flow in said blood vessel at said flow impeding member such that fluid can flow past said flow impeding member and adjacent said blood vessel selected portion; and (d) dispensing a dispersant from the catheter drug delivery region such that said dispersant flows past said flow impeding member and closely proximate said blood vessel selected portion.

33. The method as specified in claim 32 wherein said flow impeding member is an inflatable balloon with a contoured outer surface when inflated, and step (c) includes the step of disposing said contoured outer surface proximate said blood vessel selected portion to constrict flow therepast.

34. The method as specified in claim 33 further comprising the step of inflating said balloon such that a portion of said contoured outer surfaces engages said blood vessel selected portion.

* * * * *